(12) United States Patent
Sugihara et al.

(10) Patent No.: US 11,191,804 B2
(45) Date of Patent: *Dec. 7, 2021

(54) CYTOCIDAL AGENT

(71) Applicant: FUJITA ACADEMY, Aichi (JP)

(72) Inventors: Kazuhiro Sugihara, Nagoya (JP);
Naohiro Kanayama, Hamamatsu (JP);
Toshiaki Shibata, Hamamatsu (JP);
Yuichiro Onodera, Hokkaido (JP)

(73) Assignee: FUJITA ACADEMY, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/960,417

(22) PCT Filed: Dec. 28, 2018

(86) PCT No.: PCT/JP2018/048523
§ 371 (c)(1),
(2) Date: Jul. 7, 2020

(87) PCT Pub. No.: WO2019/138944
PCT Pub. Date: Jul. 18, 2019

(65) Prior Publication Data
US 2020/0330549 A1 Oct. 22, 2020

(30) Foreign Application Priority Data
Jan. 9, 2018 (JP) .............................. JP2018-001063

(51) Int. Cl.
| | | |
|---|---|---|
| *A61K 38/10* | (2006.01) | |
| *A61K 47/64* | (2017.01) | |
| *A61P 35/00* | (2006.01) | |
| *A61P 43/00* | (2006.01) | |
| *C07K 7/08* | (2006.01) | |

(52) U.S. Cl.
CPC .............. *A61K 38/10* (2013.01); *A61P 35/00* (2018.01)

(58) Field of Classification Search
CPC ......... A61K 38/10; A61K 47/64; A61P 35/00; A61P 43/00; C07K 7/08
See application file for complete search history.

(56) References Cited

U.S. PATENT DOCUMENTS 5,595,756 A * 1/1997 Bally .................... A61K 9/1272
264/4.1
9,783,576 B2 * 10/2017 Fukuda .................... C07K 7/08

2016/0145308 A1  5/2016 Fukuda et al.
2017/0290882 A1* 10/2017 Andronova ........ A61K 31/7068
2017/0360955 A1* 12/2017 Janssen .............. A61K 51/1018

FOREIGN PATENT DOCUMENTS

JP           6613499 B2    12/2019
WO    WO 2019/039540 A1   2/2019

OTHER PUBLICATIONS

Endometriosis from Merck manual, pp. 1-7. Accessed Apr. 13, 2021. (Year: 2021).*
Ovarian Cancer from Merck manual, pp. 1-12. Accessed Apr. 13, 2021. (Year: 2021).*
Hait WN, "Anticancer drug development: the grand challenges," Nature Reviews, Apr. 20, 9: 253-254. (Year: 2010).*
Sporn et al, "Chemoprevention of cancer," Carcinogenesis, 2000, 21(3): 525-530. (Year: 2000).*
Gura T, "Systems for Identifying New Drugs are Often Faulty," Science, Nov. 1997, 278: 1041-1042. (Year: 1997).*
Auerbach et al., "Angiogenesis assays: Problems and pitfalls," Cancer and Metastasis Reviews, 2000, 19: 167-172. (Year: 2000).*
Jain RK, "Barriers to Drug Delivery in Solid Tumors," Scientific American, Jul. 1994, 58-65. (Year: 1994).*
Neidel, Stephen, ed., Cancer Drug Design and Discovery, Elsevier/Academic Press, 2008, 427-431. (Year: 2008).*
Proliferation from Merck manual, pp. 1-4. Accessed Apr. 13, 2021. (Year: 2021).*
International Search Report for PCT International Patent Application No. PCT/JP2018/048523 dated Mar. 12, 2019.
International Preliminary Report on Patentability for PCT International Patent Application No. PCT/JP2018/048523 dated May 12, 2020.
Sugihara et al., "Development of pro-apoptotic peptides as potential therapy for peritoneal endometriosis", Nat. Comm., 2014, vol. 5, No. 4478, pp. 1-9.
Sugihara, "Peptide drug discovery" (non-official translation), Journal of Japan Society of Endometriosis, 2015, vol. 36, pp. 38-40.

* cited by examiner

*Primary Examiner* — Julie Ha
(74) *Attorney, Agent, or Firm* — Lathrop GPM LLP; Brian C. Trinque; Rebecca Wright

(57) ABSTRACT

An object of the present invention is to provide a peptide drug that is able to selectively induce apoptosis in target cells. The present invention is a cytocidal agent containing a fusion peptide of an endosome escape peptide and an apoptosis-inducing peptide, which consists of an amino acid sequence represented by SEQ ID NO: 1, and the said cytocidal agent as a therapeutic agent for a disease caused by abnormal proliferation of cells.

6 Claims, 4 Drawing Sheets
Specification includes a Sequence Listing.

SEQUENCE LISTING

```
<160> NUMBER OF SEQ ID NOS: 5

<210> SEQ ID NO 1
<211> LENGTH: 19
<212> TYPE: PRT
<213> ORGANISM: Artificial Sequence
<220> FEATURE:
<223> OTHER INFORMATION: Effector peptide

<400> SEQUENCE: 1
```

```
Lys Leu Ala Lys Leu Ala Lys Lys Leu Ala Lys Leu Ala Lys His Leu
1               5                   10                  15

Ala His Leu

<210> SEQ ID NO 2
<211> LENGTH: 14
<212> TYPE: PRT
<213> ORGANISM: Artificial Sequence
<220> FEATURE:
<223> OTHER INFORMATION: K14D peptide

<400> SEQUENCE: 2

Lys Leu Ala Lys Leu Ala Lys Lys Leu Ala Lys Leu Ala Lys
1               5                   10

<210> SEQ ID NO 3
<211> LENGTH: 5
<212> TYPE: PRT
<213> ORGANISM: Artificial Sequence
<220> FEATURE:
<223> OTHER INFORMATION: H5D peptide

<400> SEQUENCE: 3

His Leu Ala His Leu
1               5

<210> SEQ ID NO 4
<211> LENGTH: 28
<212> TYPE: PRT
<213> ORGANISM: Artificial Sequence
<220> FEATURE:
<223> OTHER INFORMATION: K14D-H5D-Z13 peptide

<400> SEQUENCE: 4

Lys Leu Ala Lys Leu Ala Lys Lys Leu Ala Lys Leu Ala Lys His Leu
1               5                   10                  15

Ala His Leu Val Arg Arg Ala Asp Asn Arg Pro Gly
            20                  25

<210> SEQ ID NO 5
<211> LENGTH: 25
<212> TYPE: PRT
<213> ORGANISM: Artificial Sequence
<220> FEATURE:
<223> OTHER INFORMATION: K7D-H18D peptide

<400> SEQUENCE: 5

Lys Leu Ala Lys Leu Ala Lys His Leu Ala His Leu Ala His His Leu
1               5                   10                  15

Ala His Leu Ala His His Leu Ala His
            20                  25
```

CYTOCIDAL AGENT

TECHNICAL FIELD

The present invention relates to a peptide drug that is able to selectively induce apoptosis in target cells.

Priority is claimed on Japanese Patent Application No. 2018-001063, filed Jan. 9, 2018, the content of which is incorporated herein by reference.

BACKGROUND ART

Active ingredients of pharmaceuticals are classified into low-molecular-weight drugs (low-molecular-weight compound drugs), antibody drugs, and medium-molecular-weight drugs larger than low-molecular-weight compounds and smaller than antibodies, based on their size. Medium-molecule-weight drugs include, for example, peptide drugs. Low-molecular-weight drugs, medium-molecular-weight drugs, and antibody drugs have their own advantages and disadvantages. For example, since low-molecular-weight drugs have a small molecular weight, they can pass through the cell membrane and enter the inside of the target cells, but cannot inhibit the binding between proteins. Further, although there is an advantage that the manufacturing cost is relatively low, screening has been performed for many years, and it is difficult to search for new molecules. On the other hand, antibody drugs have high specificity and binding ability to target molecules and can inhibit the binding between proteins, but their large molecular weight prevents them from passing through the cell membrane and entering the inside of target cells. Also, the high manufacturing cost is a major disadvantage. Medium-molecule-weight drugs have the advantages of both low-molecule-weight drugs and antibody drugs. That is, in addition to having high specificity and binding ability to the target molecule, they can act on the intracellular target molecule across the cell membrane. In addition, since the chemical synthesis is generally possible, the manufacturing cost is lower than that of the antibody drugs and a drug with high purity can be synthesized.

Apoptosis means cell death controlled and adjusted as a proliferation inhibition mechanism among cell deaths of multicellular organisms. In multicellular organisms, exclusion of unnecessary cells or harmful cells caused in a generation or reproduction process is performed by inducing apoptosis in the cell. In addition, by inducing apoptosis in a cell which is a cause of a disease and excluding the cell, it is possible to expect improvement in condition of the disease. In this way, substances having activity of inducing apoptosis are used for therapeutic use. For example, by inducing apoptosis in a cancer cell, it can be expected to remit or cure cancer.

As a peptide drug that induces apoptosis in cells causing a disease, for example, a peptide composition containing a fusion peptide of a Z13 peptide that is specifically expressed on the cell surface of endometriosis cells (endometrial cells that are present other than the endometrium) and specifically binds to CNGB3 (cyclic nucleotide-gated channel beta 3) which is a molecule not expressed on the peritoneal surface, and an endosome escape peptide, and a fusion peptide of a Z13 peptide and an apoptosis-inducing peptide has been reported (refer to Patent Document 1). By incorporating both peptides in an endometrial cell by the Z13 peptide moiety, it is possible to selectively induce apoptosis in an endometrial cell. In one example, a peptide composition including a fusion peptide between a Z13 peptide and an endosome escape peptide and a fusion peptide between a Z13 peptide and an apoptosis-inducing peptide was administered to the peritoneum of a baboon which had developed endometriosis via laparoscopy, selective apoptosis was induced only in a cell of a lesion of endometriosis, and apoptosis was not induced in other adjacent cells (refer to Non-Patent Document 1).

PRIOR ART LITERATURE

Patent Documents
Patent document 1: United States patent application, Publication No. 2016/145308
Non-Patent Document
Non-patent document 1: Sugihara, et al., NATURE COMMUNICATIONS, 2014, Volume 5. Article Number 4478.

DISCLOSURE OF INVENTION

Problems to be Solved by the Invention

An objective of the present invention is to provide a peptide drug that is able to selectively induce apoptosis in target cells.

The present inventors have conducted extensive studies to solve the above-mentioned problems, and as a result, found that a fusion peptide of an endosomal escape peptide consisting of a specific peptide sequence with an apoptosis-inducing peptide consisting of a specific peptide sequence is able to induce apoptosis in cancer cells with high selectivity and efficiency, and thus completed the present invention.

That is, the present invention provides the following cytocidal agent and method for treating a disease caused by abnormal cell proliferation.

Means for Solving the Problems

[1] A cytocidal agent comprising a peptide consisting of an amino acid sequence represented by SEQ ID NO: 1.
[2] The cytocidal agent according to [1], wherein the peptide consisting of the amino acid sequence represented by SEQ ID NO: 1 is
  a peptide consisting exclusively of D-amino acids,
  a peptide in which the first to the $14^{th}$ amino acids are D-amino acids in the amino acid sequence represented by SEQ ID NO: 1, and the $15^{th}$ to $19^{th}$ amino acids are L-amino acids,
  a peptide in which the first to $14^{th}$ amino acids are L-amino acids, and the $15^{th}$ to the $19^{th}$ amino acids are D-amino acids in the amino acid sequence represented by SEQ ID NO: 1, or
  a peptide consisting exclusively of L-amino acids.
[3] The cytocidal agent according to [1] or [2], which is a therapeutic agent for a disease caused by abnormal proliferation of cells.
[4] The cytocidal agent according to [3], wherein the disease is a cancer.
[5] A method for treating a disease caused by abnormal cell proliferation, comprising
  a step of administering an effective amount of the cytocidal agent according to any one of [1] to [4] to an animal that has developed a disease caused by abnormal cell proliferation.

Effects of the Invention

The cytocidal agent according to the present invention is able to induce apoptosis in target cells very efficiently.

Therefore, the cytocidal agent is particularly effective as a therapeutic agent for diseases caused by abnormal cell proliferation such as cancer.

BEST MODE FOR CARRYING OUT THE INVENTION

<Cytocidal Agent>

Figure 1:
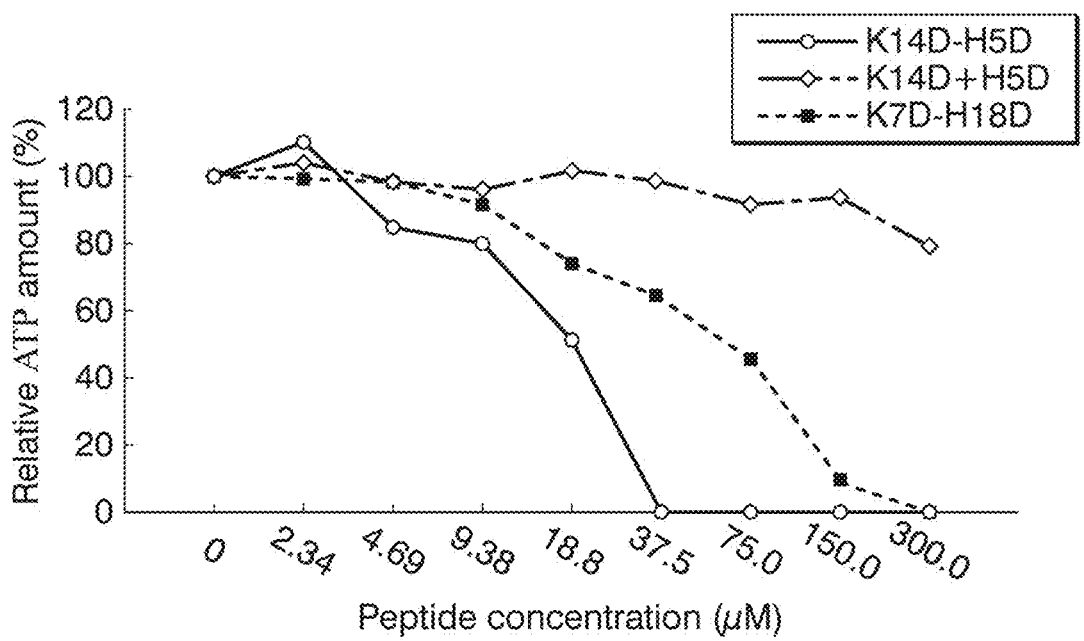
FIG. 1 A graph showing the measurement results of relative ATP amount (%) of the A431-CNGB3-myc cells treated with each peptide in Example 1.

The cytocidal agent according to the present invention contains a peptide (hereinafter, may also referred to as "effector peptide") consisting of the amino acid sequence represented by SEQ ID NO: 1 (KLAKLAKKLAKHLAHL). The effector peptide is a peptide in which a peptide having apoptosis-inducing activity and a peptide having endosomal escape activity are linked in tandem. Since the cytocidal agent according to the present invention is sufficiently small, it can be incorporated into the target cells by endocytosis without a specific uptake system. Then, the cytocidal agent encapsulated with the endosome incorporated into the target cells is released into the cytoplasm of the target cells as a result of breaking the endosomal membrane by the action of the peptide moiety having an endosomal escape activity. The cytocidal agent released into the cytoplasm damages the mitochondrial membrane by the action of the peptide moiety having apoptosis-inducing activity, and induces apoptosis of the target cells.

The cytocidal agent according to the present invention contains, in one molecule, a peptide moiety having apoptosis-inducing activity and a peptide moiety having endosomal escape activity. Therefore, compared to the peptide composition that contains a peptide having apoptosis-inducing activity alone, or a peptide having endosomal escape activity alone, apoptosis can be induced very efficiently in the target cells.

In the present invention and the specification of the present application, the "target cells" are the objective cells for which apoptosis is desired to be induced.

As disclosed in Patent Document 1, the peptide (hereinafter, sometimes referred to as "KLAK peptide") consisting of an amino acid sequence (hereinafter sometimes referred to as "KLAK sequence") that is formed by repeating four amino acids of KLAK has an action of inducing apoptosis by damaging the mitochondrial membrane (apoptosis inducing activity). The peptide (hereinafter, sometimes referred to as "HLAH peptide") consisting of an amino acid sequence (hereinafter, sometimes referred to as "HLAH sequence") that is formed by repeating four amino acids of HLAH has an action of breaking the endosome membrane (endosomal escape activity). The peptide in which the KLAK peptide and the HLAH peptide are linked has endosomal escape activity and apoptosis-inducing activity, and the strength of the activities are affected by the length of the amino acid in each peptide and the linking order of the two peptides.

The effector peptide consisting of an amino acid sequence represented by SEQ ID NO: 1 is a peptide in which an HLAH sequence consisting of 5 amino acids is linked to a downstream of the KLAK sequence consisting of 14 amino acids. That is, in the amino acid sequence of SEQ ID NO: 1, the first to the $14^{th}$ amino acids are sites having apoptosis-inducing activity and the $15^{th}$ to the $19^{th}$ amino acids are sites having endosome escape activity. In order to obtain the highest apoptosis-inducing activity in a case of being taken into the target cell, the effector peptide is a peptide in which the length of the KLAK sequence, the length of the HLAH sequence, and the order of linkage of the KLAK sequence and the HLAH sequence are optimized. Since the cytocidal agent has the effector peptide, the cytocidal agent according to the present invention has very high apoptosis-inducing activity.

The effector peptide included in the cytocidal agent according to the present invention is not particularly limited as long the peptide is a peptide consisting of an amino acid sequence represented by SEQ ID NO: 1, may be a peptide consisting of an L-amino acid, may be a peptide consisting of a D-amino acid, or may be a peptide consisting of an L-amino acid and a D-amino acid. Since stability is high in the endosome and higher apoptosis-inducing activity is obtained, the effector peptide is preferably a peptide consisting of at least some D-amino acids, at least one of the KLAK sequence (in the amino acid sequence represented by SEQ ID NO: 1, the first to the $14^{th}$ amino acids) and the HLAH sequence (in the amino acid sequence represented by SEQ ID NO: 1, the $15^{th}$ to the $19^{th}$ amino acids) is more preferably a peptide consisting of a D-amino acid, and all thereof are particularly preferably a peptide consisting of a D-amino acid.

The cytocidal agent according to the present invention may have other biomolecules linked to the effector peptide as long as the effect of the effector peptide consisting of the amino acid sequence represented by SEQ ID NO: 1 is not impaired. Examples of the said other biomolecules include peptides. However, it is preferable that the total size of the cytocidal agent be such that it can be incorporated into the cells by endocytosis without a specific uptake system. Specifically, the moiety other than the effector peptide is preferably 1 to 15 peptides, more preferably 1 to 10 peptides. When the cytocidal agent according to the present invention contains a moiety other than the effector peptide consisting of the amino acid sequence represented by SEQ ID NO: 1, the moiety other than the effector peptide may be on the N-terminal side or on the C-terminal side of the effector peptide.

The cytocidal agent according to the present invention is effective as a therapeutic agent for diseases caused by abnormal proliferation, and is particularly preferable as a therapeutic agent for cancer and endometriosis. The type of cancer to be treated by the cytocidal agent according to the present invention includes, but is not particularly limited to, uterine cancer, cervical cancer, pelvic cavity cancer, ovarian cancer, breast cancer, abdominal wall tumor, omental tumor esophageal cancer, stomach cancer, small intestine cancer, colon cancer, rectal cancer, cecal cancer, gallbladder cancer, pancreatic cancer, liver cancer, spleen cancer, kidney cancer, tongue cancer, pharyngeal cancer, nose cancer, parotid adenocarcinoma, thyroid cancer, malignant lymphoma, bone tumor, skin cancer, lung cancer, mediastinal cancer, testicular cancer, prostate cancer, bladder cancer, brain tumor and the like. Further, it may be a primary cancer or a metastatic cancer.

As shown in the Examples below, the cytocidal agent according to the present invention is able to induce apoptosis with high efficiency in cells with abnormal proliferation. The reason for this is not clear, but it is presumed as follows. Generally, the cells with abnormal proliferation have a high activity themselves and have a high activity of incorporating various substances from the outside by endocytosis. Therefore, it may be considered that the cytocidal agent according to the present invention administered in-vivo is preferentially taken up by the cells with abnormal proliferation to induce apoptosis rather than the normal cells.

When the cytocidal agent according to the present invention is used as a pharmaceutical drug, the administration route is not particularly limited, and may be appropriately determined depending on the target cells and the tissues containing the target cells. For example, the administration route of the cytocidal agent according to the present invention may be oral administration, intravenous administration, intraperitoneal administration, enema administration or the like.

The diseases caused by the abnormal proliferation can be treated by administering an effective amount of the cytocidal agent according to the present invention to animals having a disease caused by abnormal cell proliferation. The effective amount of the cytocidal agent may be an amount that can reduce the amount of the target cells (abnormally proliferated cells) in the animal body administered with the cytocidal agent as compared with the case where the cytocidal agent is not administered, and preferably an amount that does not cause serious side effects due to the cytocidal agent. The effective amount of the cytocidal agent can be experimentally determined in consideration of the type of the target cells, the type of animals to be administered, the administration method and the like. For example, when the cytocidal agent is administered to an animal that has developed a disease caused by abnormal proliferation of cells such as cancer, the effective amount can be determined to an amount such that the amount of the cells with abnormal proliferation in the body of the said animal is preferably reduced to 90% or less, more preferably reduced to 80% or less, even more preferably reduced to 75% or less, still even more preferably reduced to 50% or less, as compared to that of the animal without administration.

The cytocidal agent according to the present invention can be formulated as an oral solid agent such as a powder, a granule, a capsule, a tablet, and a chewable agent, an oral liquid agent such as a solution agent and a syrup agent, an injection, an enema agent, a spray agent, a patch, and an ointment by a general method.

The cytocidal agent according to the present invention is formulated by being mixed with an excipient, a binding agent, a lubricant, a disintegrating agent, a fluidizing agent, a solvent, a solubilizing agent, a buffer, a suspending agent, an emulsifier, an isotonizing agent, a stabilizer, an antiseptic agent, an anti-oxidant, a flavoring agent, a coloring agent, and the like, depending on the formulation necessity.

Examples of the excipient include saccharides such as lactose, glucose, and D-mannitol, celluloses such as starch and crystalline cellulose, sugar alcohols such as erythritol, sorbitol, and xylitol, dicalcium phosphate, calcium carbonate, and kaoline. Examples of the binding agent include pregelatinized starch, gelatin, Arabic rubber, methyl cellulose, carboxy methyl cellulose, sodium carboxy methyl cellulose, crystalline cellulose, D-mannitol, trehalose, hydroxy propyl cellulose, hydroxy propyl methyl cellulose, polyvinyl pyrrolidone, polyvinyl alcohol, and the like. Examples of the lubricant include stearic acid, calcium stearate, talc, sucrose fatty acid ester, polyethylene glycol, and the like. Examples of the disintegrating agent include crosslinking polyvinyl pyrrolidone (crospovidone), low substitution degree hydroxy propyl cellulose, starch, alginic acid, sodium alginate, and the like. Examples of the fluidizing agent include silicic acid, silicic anhydride, aluminum silicate, calcium silicate, a magnesium metasilicate aluminate compound, an aluminum oxide, an aluminum hydroxide, a magnesium oxide, a magnesium hydroxide, and the like. Examples of the solvent include purified water, a physiological saline solution, and the like. Examples of the solubilizing agent include dextran, polyvinyl pyrrolidone, sodium benzoate, ethylene diamine, salicylate amide, nicotinic acid amide, a polyoxy ethylene hydrogenated castor oil derivative, and the like. Examples of the buffer include sodium citrate hydrate, sodium acetate hydrate, sodium hydrogen carbonate, trometamol, boric acid, borax, dibasic sodium phosphate hydrate, sodium dihydrogen phosphate, and the like. Examples of the suspending agent or the emulsifier include sodium lauryl sulfate, Arabic rubber, gelatin, lecithin, glyceryl monostearate, polyvinyl alcohol, polyvinyl pyrrolidone, celluloses such as sodium carboxy methyl cellulose, polyoxy ethylene hydrogenated castor oil, and the like. Examples of the isotonizing agent include saccharides such as lactose, glucose, and D-mannitol, sodium chloride, potassium chloride, glycerin, propylene glycol, polyethylene glycol, urea, and the like. Examples of the stabilizer include polyethylene glycol, sodium dextran sulfate, sodium sulfite, and the like. Examples of the antiseptic agent include para-hydroxybenzoic esters, chlorobutanol, benzyl alcohol, phenethyl alcohol, chlorocresol, dehydroacetic acid, sorbic acid, and the like. Examples of the anti-oxidant include sulfite, ascorbic acid, and the like. Examples of the flavoring agent include sweeteners generally used in the field of the therapeutic drug and the food, aromatic chemical, and the like. Examples of the coloring agent include coloring materials generally used in the field of the therapeutic drug and the food.

The cytocidal agent according to the present invention may be used as it is, and can be also used as a therapeutic composition including other components. Examples of the other components included in the therapeutic composition include the excipient, the binding agent, the lubricant, the disintegrating agent, the fluidizing agent, the solvent, the solubilizing agent, the buffer, the suspending agent, the emulsifier, the isotonizing agent, the stabilizer, the antiseptic agent, the anti-oxidant, the flavoring agent, the coloring agent, and the like. In addition, the therapeutic composition may contain other effective components than the cytocidal agent according to the present invention.

The cytocidal agent according to the present invention is preferably administered to mammals, more preferably administered to humans or livestock such as mouse, rat, rabbit, guinea pig, hamster, monkey, sheep, horse, cattle, pig, donkey, dog, and cat, and further more preferably administered to humans.

EXAMPLES

Subsequently, the present invention will be further explained in detail using examples. The present invention is not limited to the following examples.

The endometriosis model cells and endometriosis model mice used in the following experiments were prepared as follows.

<Endometriosis Model Cell (A431-CNGB3-Myc Cell)>

A transformed cell (A431-CNGB3-myc cell) obtained by introducing a gene encoding human CNGB3, in which an myc tag was fused in a C-terminal, into an A431 cell (human epithelial-like cell cancer-derived cell strain) and forcibly expressing thereof was prepared as an endometriosis model cell.

Culturing of the A431-CNGB3-myc cells was performed at 37° C. in a 5 volume % carbon dioxide environment using a medium in which 10% of inactivated FBS (fetal bovine serum, manufactured by Corning Corporation) and 1% of penicillin-streptomycin (manufactured by Invitrogen Corporation) were contained in a DMEM High Glucose medium (manufactured by GIBCO Corporation), as a culture medium. Passages were performed every two to three days.

<Endometriosis Model Mouse>

The A431-CNGB3-myc cells were transplanted to a peritoneal cavity of an immunodeficient mouse (NOD/ShiJic-scid Jcl strain, supplied by CLEA Japan, Inc.) to prepare an endometriosis model mouse.

Specifically, after thawing the frozen-stored A431-CNGB3-myc cells, a cell solution prepared by adding a culture medium to cells passaged twice using a 10-cm dish (Lot No. F3BAXQ103, manufactured by Thermo Fisher Scientific Co., Ltd.) so as to be $1 \times 10^6$ cells/0.5 mL/body was used as an administration solution. The administration solution was intraperitoneally administered to a 7-week-old female immunodeficient mouse as soon as possible after preparation to transplant the A431-CNGB3-myc cells.

For the mouse, 5 to 10 mice/cage in a polycarbonate cage (W×D×H=270×440×187 (mm)) were bred in an environment of 19.8° C. to 27.1° C., humidity of 32% to 75%, and 12 hours of light. Feed (sterilized CRF-1 (solid type), manufactured by Oriental Yeast Co., Ltd.) and drinking water (sterile tap water) were freely ingested.

Model preparation was confirmed by observation and collection of peritoneal tumor. One to three weeks after the A431-CNGB3-myc cell transplantation, autopsy was performed on two mice each week to visually check whether a tumor (granular shape of about 1 mm) was observed in the peritoneum and photographed. Thereafter, the peritoneum was collected, and 4 locations (each on the left and right sides of the abdomen and back) were cut out, immersed and fixed in 10% neutral buffer formalin, respectively, and refrigerated. The peritoneum after formalin fixation was subjected to immunohistochemical staining using an anti-c-myc antibody to examine the status of dissemination.

As a result of visual checking of the mouse after the A431-CNGB3-myc cell transplantation, in the first test, although a tumor was visually confirmed one week after transplantation, no peritoneal dissemination was observed, but two or three weeks after transplantation, a tumor and peritoneal dissemination were visually confirmed. In the second test, peritoneal dissemination was visually confirmed even one week after transplantation. In addition, as a result of c-myc staining of the peritoneal tissue fragment of the mouse after transplantation, it was confirmed that one week after the transplantation, peritoneal dissemination had already proceeded.

<Mouse with Luciferase Gene-Transferred Subcutaneous Tumor Bearing Ovarian Cancer (OVCAR3-Luc Mouse)>

The tumor tissue to be transplanted to the mouse was prepared by culturing an ovarian cancer cell line (OVCAR3-Luc cells, transferred from another facility) into which the luciferase gene had been introduced, and used. The OVCAR3-Luc cells were cultured in a culture medium containing a RPMI medium 1640 (11875-093: manufactured by Gibco) containing 10% inactivated FBS (manufactured by Corning) at 37° C. and under a 5 vol % carbon dioxide environment. Passaging was carried out every 2-3 days.

The OVCAR3-Luc cell line was detached by trypsin treatment, and the cell solution prepared by adding the culture medium so as to have $5 \times 10^5$ cells/100 μL/body was used as the administration solution. This administration solution was subcutaneously administered to the back of 8 to 10-week-old female SCID mice as soon as possible after the preparation, thereby preparing the subcutaneous tumor model mice in which the OVCAR3-Luc cells were subcutaneously transplanted.

Example 1

The cytocidal activity of each peptide was examined for two types of cancer cells (A431-CNGB3-myc cells and OVCAR3-Luc cells) with enhanced cell proliferation ability. The amino acid sequences of the peptides used are shown in Table 1. Among the peptides listed in Table 1, the K14D-H5D peptide is a peptide having the amino acid sequence represented by SEQ ID NO: 1, which is consisting exclusively of D-amino acids. The K14D peptide is a KLAK peptide consisting exclusively of D-amino acids, and the H5D peptide is an HLAH peptide consisting exclusively of D-amino acids. The K14D-H5D-Z3 peptide is a peptide obtained by adding a Z13 peptide consisting of L-amino acids to the C-terminal of the K14D-H5D peptide. The K7D-H18D peptide is a peptide consisting of the amino acid sequence represented by SEQ ID NO: 5, which is consisting exclusively of D-amino acids.

TABLE 1

| Peptide | Seq. | Seq. No. |
|---|---|---|
| K14D-H5D | KLAKLAK-KLAKLAK-HLAHL | 1 |
| K14D | KLAKLAK-KLAKLAK | 2 |
| H5D | HLAHL | 3 |
| K14D-H5D-Z13 | KLAKLAK-KLAKLAK-HLAHL-VRRADNRPG | 4 |
| K7D-H18D | KLAKLAK-HLAHLAH-HLAHLAH-HLAH | 5 |

<Evaluation of Cytocidal Activity>

The cytocidal activity of each peptide was evaluated by measuring the ATP amount in the cells treated with each peptide using CellTiter-Glo (registered trademark) assay kit (manufactured by Promega).

Specifically, first, the A431-CNGB3-myc cells or the OVCAR3-Luc cells after 3 to 4 passages were seeded in a 96-well plate (manufactured by Corning/Costar, Lot No. 00515003) so as to adjust the cell concentration to $1\times10^4$ cells/well. After culturing for 2 days from seeding, each peptide was added to each well at a final concentration of 0 (no peptide added), 2.34, 4.69, 9.38, 18.8, 37.5, 75.0, 150.0 or 300.0 µM followed by culturing for 24 hours. Further, the K14D peptide was combined with the H5D peptide, and the resulting mixture of both peptides was added to each well. Then, the culture supernatant was removed from each well, the CellTiter-Glo buffer was added to the remaining cells and homogenized, and then the supernatant was collected by centrifugation to obtain a lysate. To this lysate, a double amount of PBS and the same amount of 2× CellTiter Glo Reagent as the lysate were added and stirred to prepare a reaction solution, and the reaction solution was allowed to stand at room temperature for 10 minutes. Luminescence (RLU: RELATIVE LIGHT UNITS) of each reaction solution after standing at room temperature was measured using a Synergy H1 hybrid multimode microplate reader (manufactured by BioTek). The luminescence intensity of the reaction solution is an index of the ATP amount. The smaller the luminescence intensity of the reaction solution, the smaller the ATP amount and the stronger the cytocidal activity of the administered peptide. All trials were measured in triplicate, and the average value thereof was taken as the emission intensity (RLU) of each reaction solution.

Figure 2:
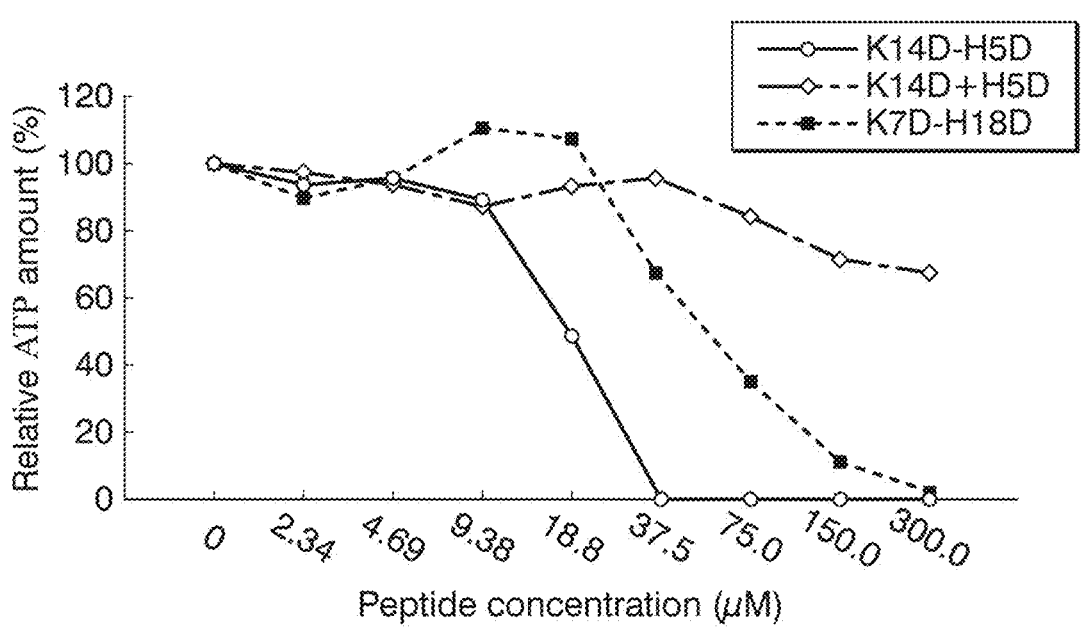
FIG. 2 A graph showing the measurement results of relative ATP amount (%) of the OVCAR3-Luc cells treated with each peptide in Example 1.
Figure 3:
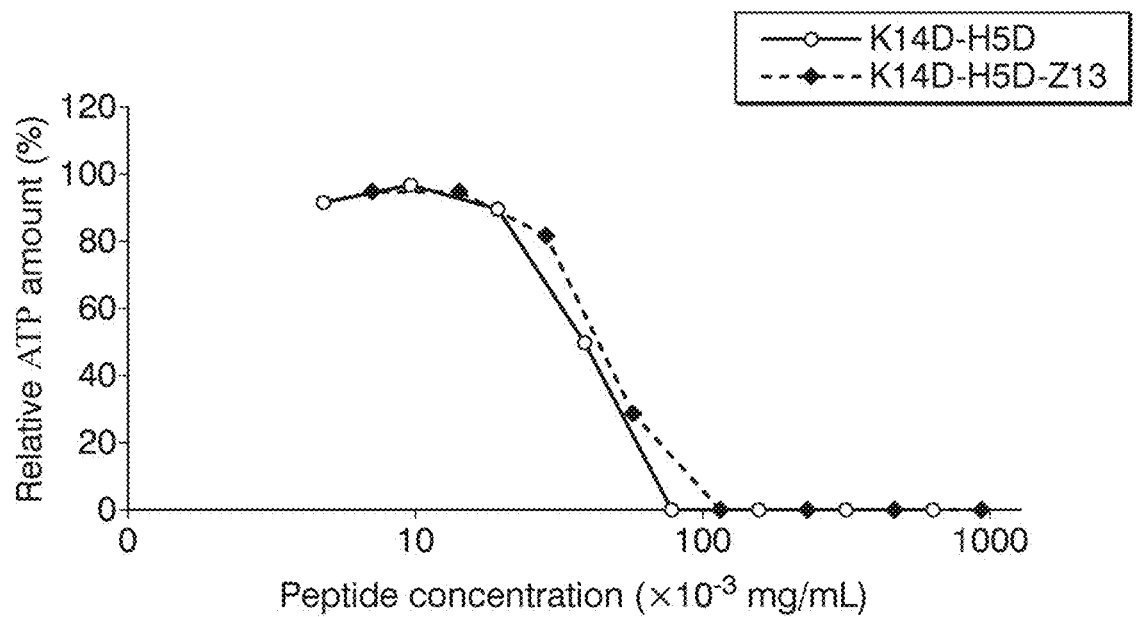
FIG. 3 A graph showing the measurement results of relative ATP amount (%) of OVCAR3-Luc cells treated with each peptide in Example 1.

The relative luminescence intensity (%) of each reaction solution was calculated taking the luminescence intensity (RLU) of the reaction solution without the peptide as a base of 100%, and taken as the relative ATP amount (%). The relative ATP amount (%) of the A431-CNGB3-myc cells treated with each peptide is shown in FIG. 1, and the relative ATP amount (%) of the OVCAR3-Luc cells treated with each peptide is shown in FIGS. 2 and 3, respectively. In the figures, "K14D+H5D" indicates the relative ATP amount (%) of the reaction solution to which both the K14D peptide and the H5D peptide were added.

As shown in FIGS. 1 and 2, in the case where both the K14D peptide and the H5D peptide were added, no cytocidal activity was observed on any of the cancer cells, even if the added amount of each peptide was 300 µM. In contrast, the K14D-H5D peptide and the K7D-H18D peptide, which are fusion peptides of the KLAK peptide and the HLAH peptide, showed a relative ATP amount decreased in a dose-dependent manner, and cytocidal activity. The K14D-H5D peptide was apparently stronger in cytocidal activity than the K7D-H18D peptide in any of the cancer cells. Further, as shown in FIG. 3, the K14D-H5D peptide and the K14D-H5D-Z13 peptide showed the same cytocidal activity on the OVCAR3-Luc cells having no CNGB3 on the cell surface. That is, it was confirmed that even a peptide in which another peptide was linked to the K14D-H5D peptide had cytocidal activity as long as it had a size able to be incorporated by endocytosis.

<TUNEL Staining>

TUNEL (TdT-mediated dUTP nick end labeling) staining was performed on the A431-CNGB3-myc cells treated with 300 µM of the K14D-H5D peptide and the A431-CNGB3-myc cells not treated with the peptide. As a result, in the A431-CNGB3-myc cells treated with the K14D-H5D peptide, the nuclei of almost all cells were stained brown (TUNEL positive), and there were apparently fewer cells compared with the A431-CNGB3-myc cells not treated with the peptide. On the other hand, in the A431-CNGB3-myc cells not treated with the peptide, brown cells were not found in the nucleus. From these results, it was confirmed that the K14D-H5D peptide induces apoptosis and exhibits a cytocidal effect.

Example 2

The K14D-H5D peptide used in Example 1 was administered to endometriosis model mice, and the cytocidal activity on endometrial cells was examined.

<Single Intraperitoneal Administration of Peptide>

Seven days after the A431-CNGB3-myc cells were intraperitoneally transplanted, 0.5 mL of physiological saline solution warmed to 37° C. was intraperitoneally administered to an endometriosis model mouse under isoflurane anesthesia, followed by performing massage. Immediately after the massage, a solution of the K14D-H5D peptide dissolved in physiological saline was intraperitoneally administered. The K14D-H5D peptide was administered at a dose of 0 mg/10 mL/kg (control) (n=7), 5 mg/10 mL/kg (n=8), or 10 mg/10 mL/kg (n=8) per mouse body weight <Collection of Peritoneum (Sample Collection)>

The endometriosis model mouse to which the K14D-H5D peptide was administered was exsanguinated to death under isoflurane anesthesia 24 hours after the peptide administration, and the peritoneum was collected. The peritoneum for ATP measurement was frozen in liquid nitrogen and then stored in a deep freezer until measurement. The peritoneum for preparing a pathological specimen was immersed in 10% neutral buffered formalin, fixed, and then stored in a refrigerator.

<Measurement of Weight>

Each mouse was weighed 7 days after the A431-CNGB3-myc cells were intraperitoneally transplanted, before K14D-H5D peptide administration and before exsanguination.

The mouse group in which the dose of the K14D-H5D peptide per mouse body weight was 0 mg/10 mL/kg was represented as G1 group, the mouse group in which the dose of the K14D-H5D peptide per mouse body weight was 5 mg/10 mL/kg was represented as G2 group, and the mouse group in which the dose of the K14D-H5D peptide per mouse body weight was 10 mg/10 mL/kg was represented as G3 group. Table 2 shows the measurement results (means standard error) of each group. In the Table, "7th day" in the "Body Weight" column is the body weight 7 days after the intraperitoneal transplantation of the A431-CNGB3-myc cells, which was before the administration of the K14D-H5D peptide, and "8th day" is the body weight 24 hours after the administration of the K14D-H5D peptide.

TABLE 2

| Mouse Group | Body Weight (g) | |
|---|---|---|
|  | 7th day | 8th day |
| G1 | 20.1 ± 0.6 | 19.7 ± 0.5 |
| G2 | 20.1 ± 0.4 | 19.2 ± 0.5 |
| G3 | 20.0 ± 0.4 | 17.5 ± 0.3 |

As shown in Table 2, a slight decrease in the body weight was observed depending on the dose of the K14D-H5D peptide, but this decrease was small. From these results, it was found that the K14D-H5D peptide had a small effect on normal cells, and therefore the peptide could be administered to animals relatively safely.

<ATP Amount Measurement>

The ATP amount was measured using CellTiter-Glo (registered trademark) Assay Kit (manufactured by Promega).

The weight of the frozen peritoneum was measured, and CellTiter-Glo buffer in an amount 10 times as much as that of the frozen tissue was added to be homogenized, and then the supernatant was collected by centrifugation to obtain a lysate. To this lysate, a double amount of PBS and the same amount of 2× CellTiter Glo Reagent as the lysate were added and stirred to prepare a reaction solution, and the reaction solution was allowed to stand at room temperature for 10 minutes. Luminescence (RLU) of each reaction solution after standing at room temperature was measured using a Synergy H1 hybrid multimode microplate reader (manufactured by BioTek). All trials were measured in triplicate (n=3), and the average value thereof was taken as the measurement value of the emission intensity (RLU) of each reaction solution.

Figure 4:
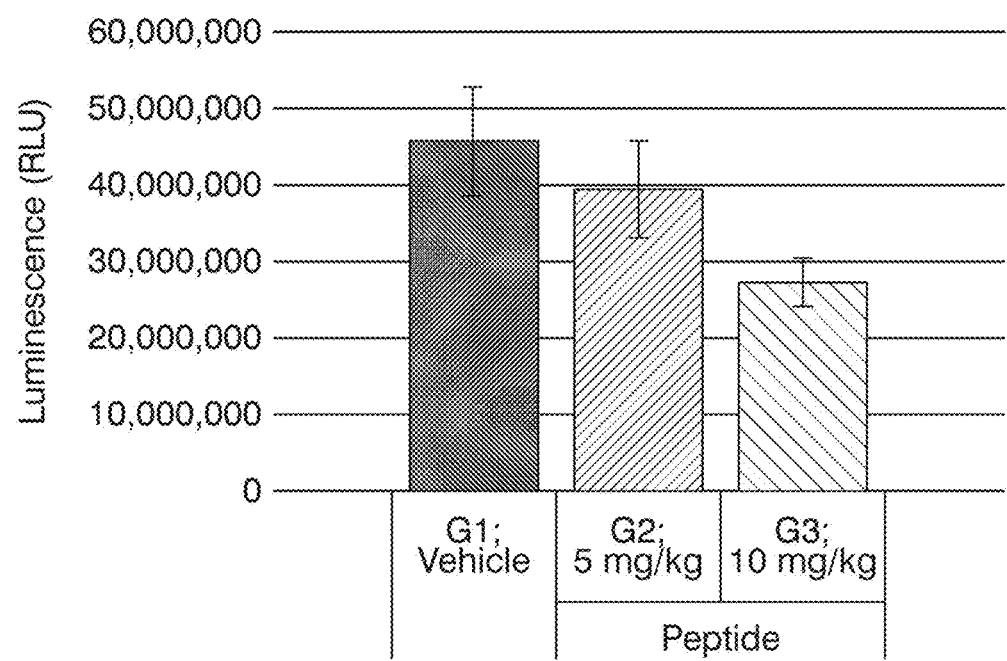
FIG. 4 A graph showing the measurement results of luminescence intensity (RLU) of peritoneum of the endometriosis model mice intraperitoneally administered with the K14D-H5D peptide once in Example 2.

FIG. 4 shows the measurement results (means±standard error) of the ATP amount in each group. It was confirmed that the luminescence intensity (RLU) of the peritoneum was decreased in a dose-dependent manner of the administered K14D-H5D peptide, and that the ATP amount of the peritoneum was decreased. The decrease in the ATP amount in the peritoneum means a decrease in the number of surviving A431-CNGB3-myc cells transplanted into the peritoneum. From these results, it was confirmed that the K14D-H5D peptide kills the A431-CNGB3-myc cells in the abdominal cavity, in other words, the K14D-H5D peptide exerts cytocidal effect in the in-vivo environment.

Example 3

The K14D-H5D peptide used in Example 1 was intravenously administered to the OVCAR3-Luc mouse, and the cytocidal activity on cancer cells was examined.
<Tail Vein Administration of Peptide>
Fourteen days after subcutaneously transplanting the OVCAR3-Luc cells, 50 μL of a solution prepared by dissolving the K14D-H5D peptide in physiological saline was administered once a day for six consecutive days to the OVCAR3-Luc mouse through the tail vein. The K14D-H5D peptide was administered so that the dose per mouse body weight was 0 μmol/kg/day (control) or 1.17 μmol/kg/day.
<Measurement of Tumor Tissue Size>
Luminescence imaging test was performed on each mouse, and the photon number of the tumor on the back and the size of the tumor tissue were measured over time.
(1) Measurement of Photon Number
Photon number was measured by an in-vivo luminescence imaging device using the luciferin-luciferase luminescence mechanism. First, the OVCAR3-Luc mouse was sedated by isoflurane inhalation anesthesia, and 100 μL of D-luciferin potassium solution (solution of D-luciferin potassium (126-05116: manufactured by Wako Pure Chemical Industries, Ltd.) dissolved in PBS at a final concentration of 30 mg/mL) was administered to the abdominal cavity. Fifteen minutes after the administration, the mouse was subject to the measurement with an in-vivo luminescence imaging device, and the photon number was measured. As the in-vivo luminescence imaging device. IVIS Imaging System (IVIS200: manufactured by Sumisho Pharma International), which is an in-vivo imaging device for optical quantification using an ultra-sensitive cooled CCD camera, was used.
(2) Measurement of Tumor Volume
The estimated tumor volume ($mm^3$) on the back of each OVCAR3-Luc mouse was calculated from the major and minor diameters of the tumor by the following equation. The major axis (mm) and the minor axis (mm) of the tumor were measured using a caliper.

[Estimated tumor volume ($mm^3$)]=[major axis (mm)]×[minor axis (mm)]×[minor axis (mm)]×½

Figure 5:
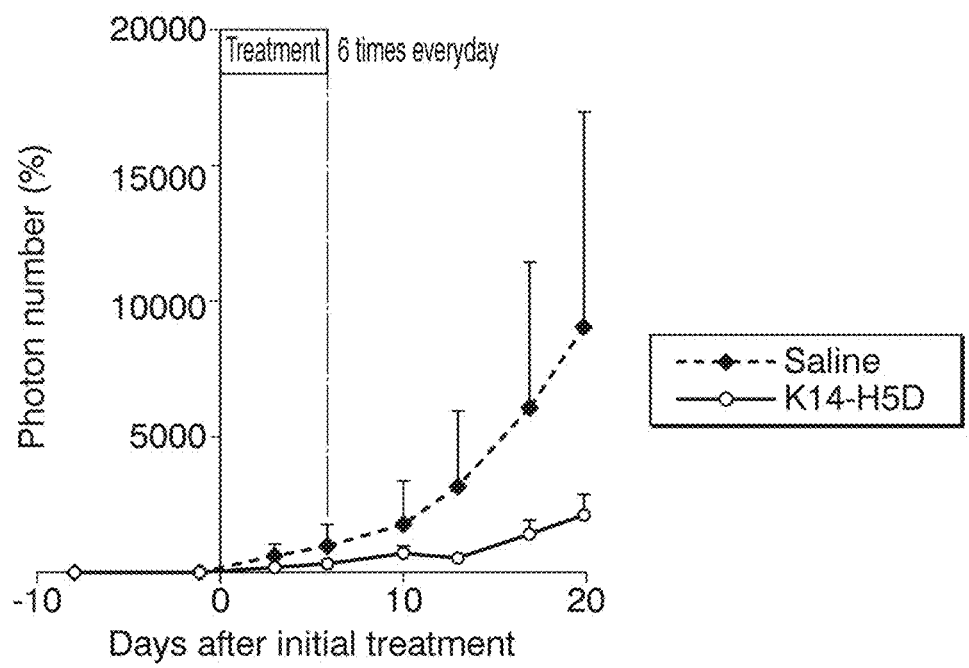
FIG. 5 A graph showing the results of time-dependent measurement of the increase rate (%) in photon number in the OVCAR3-Luc mouse administered with the K14D-H5D peptide in Example 3.
Figure 6:
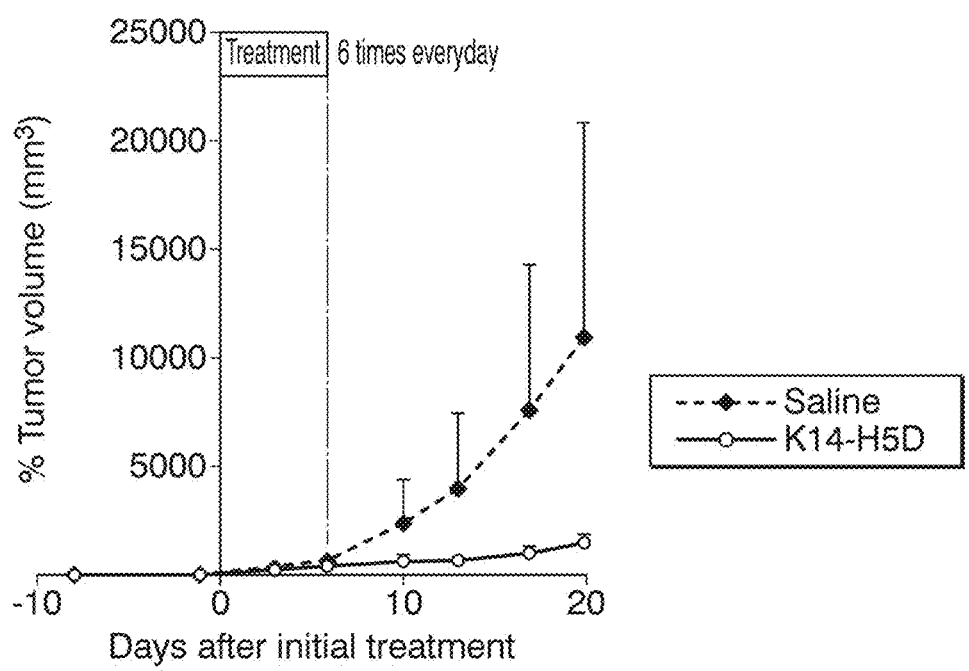
FIG. 6 A graph showing the results of time-dependent measurement of the increase rate (%) in tumor volume of the OVCAR3-Luc mouse administered with the K14D-H5D peptide in Example 3.

FIG. 5 shows the time-dependent change of the increase rate (%) of the photon number in the back tumor of each mouse, and FIG. 6 shows the time-dependent change of the increase rate (%) of the tumor volume ($mm^3$) in the back of each mouse. In both the increase rate of the photon number and increase rate of tumor volume, the value on the day before the start of administration of the peptide solution was taken as the standard (100%). In the figures, "treatment" indicates a treatment period in which the peptide solution was intravenously administered. Moreover, in both the figures, the error bars present on only the upper side indicate the standard errors (SEM). As shown in FIG. 5, the K14D-H5D peptide-administered mouse showed almost no increase in photon number and almost no increase in tumor volume. From these results, it can be found that administration of the K14D-H5D peptide can kill the tumor tissue in-vivo, and the peptide is useful as an anticancer agent.
<Measurement of Survival Rate>
The survival rate of each mouse was calculated by defining the case where the tumor growth measured by the photon number measurement reached 10 times or 20 times as compared with the measured value on the day before the peptide administration as a condition of euthanasia. The observation was carried out for 20 days, and the survival curve was analyzed by the Kaplan-Meier method.

Figure 7:
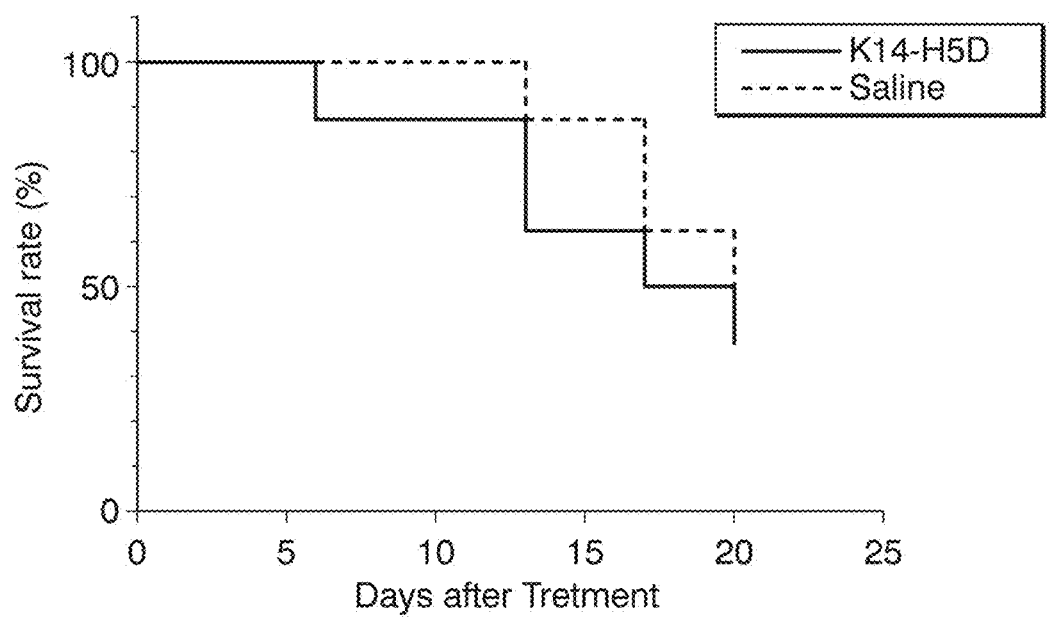
FIG. 7 A graph showing the time-dependent change of the survival rate of the OVCAR3-Luc mouse administered with the K14D-H5D peptide in Example 3 under the condition of euthanasia when the tumor growth rate reached 10 times.
Figure 8:
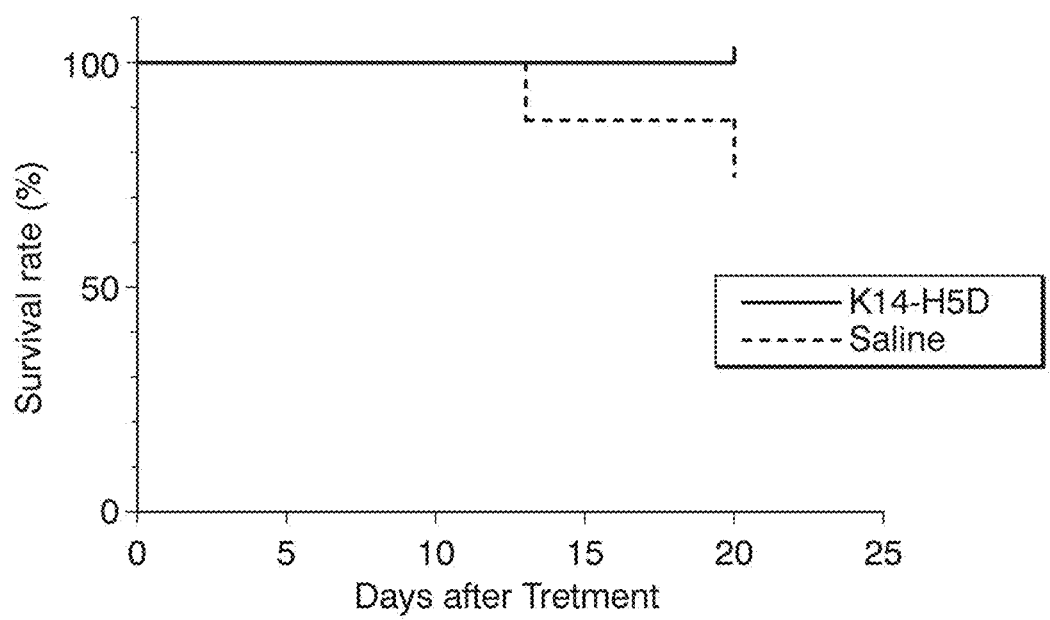
FIG. 8 A graph showing the time-dependent change of the survival rate of the OVCAR3-Luc mouse administered with the K14D-H5D peptide in Example 3 under the condition of euthanasia when the tumor growth rate reached 20 times.

FIG. 7 shows the time-dependent change of the survival rate when defining the case where the tumor growth rate reached 10 times as a condition of euthanasia, and FIG. 8 shows the time-dependent change of the survival rate when defining the case where the tumor growth rate reached 20 times as a condition of euthanasia. As shown in FIGS. 7 and 8, the survival rate of the OVCAR3-Luc mouse was significantly improved by administration of the K14D-H5D peptide, and it was recognized that the K14D-H5D peptide had a remarkable antitumor effect.
[SEQUENCE LIST]

The invention claimed is:

1. A cytocidal agent comprising a peptide comprising the amino acid sequence of SEQ ID NO: 1 with or without other biomolecules on the N-terminal side or on the C-terminal side of the peptide, wherein the C-terminal of the peptide is not linked to an alanine.

2. The cytocidal agent according to claim 1, wherein the peptide comprising the amino acid sequence of SEQ ID NO: 1 is
- a peptide comprising exclusively D-amino acids,
- a peptide in which the first to the 14$^{th}$ amino acids are D-amino acids in the amino acid sequence of SEQ ID NO: 1, and the 15$^{th}$ to 19$^{th}$ amino acids are L-amino acids,
- a peptide in which the first to 14$^{th}$ amino acids are L-amino acids, and the 15$^{th}$ to the 19$^{th}$ amino acids are D-amino acids in the amino acid sequence of SEQ ID NO: 1, or
- a peptide comprising exclusively L-amino acids.

3. The cytocidal agent according to claim 1, wherein the cytocidal agent induces apoptosis in cells and is a therapeutic agent for a disease caused by abnormal proliferation of cells.

4. The cytocidal agent according to claim 3, wherein the disease is an endometriosis or ovarian cancer.

5. The cytocidal agent according to claim 3, wherein the disease is a cancer expressing cyclic nucleotide-gated channel beta 3(CNGB3).

6. A method for treating a disease caused by abnormal cell proliferation, comprising
- a step of administering an effective amount of the cytocidal agent according to claim 1 to an animal that has developed a disease caused by abnormal cell proliferation, wherein the cytocidal agent induces apoptosis in cells.

* * * * *